(12) United States Patent
Kim

(10) Patent No.: US 6,977,296 B2
(45) Date of Patent: Dec. 20, 2005

(54) HUMAN CERVICAL CANCER SUPPRESSOR PROTEIN, POLYNUCLEOTIDE ENCODING THE PROTEIN, CELL TRANSFORMED WITH THE POLYNUCLEOTIDE AND METHOD FOR SUPPRESSING PROLIFERATION OF CANCER CELL USING THE EXPRESSION VECTOR

(76) Inventor: Jin-Woo Kim, Hyundai Apt. 118-804, Apkujung-dong, Kangnam-ku, Seoul (KR), 135-110

( * ) Notice: Subject to any disclaimer, the term of this patent is extended or adjusted under 35 U.S.C. 154(b) by 93 days.

(21) Appl. No.: 10/257,819

(22) PCT Filed: Dec. 4, 2000

(86) PCT No.: PCT/KR00/01406

§ 371 (c)(1),
(2), (4) Date: Oct. 11, 2002

(87) PCT Pub. No.: WO01/81387

PCT Pub. Date: Nov. 1, 2001

(65) Prior Publication Data

US 2004/0086974 A1 May 6, 2004

(30) Foreign Application Priority Data

Apr. 25, 2000 (KR) .......................................... 2000-21897

(51) Int. Cl.[7] .......................... C07H 21/00; C07H 21/02; C07H 21/04
(52) U.S. Cl. ..................... 536/23.5; 536/23.1; 514/44; 424/93.1; 435/320.1
(58) Field of Search .............................. 536/23.1, 23.5; 514/44; 424/93.1; 435/320.1

(56) References Cited

PUBLICATIONS

Deonarain (1998) Exp. Opin. Ther. Pat., 8(1): 53–69.*
Gorecki (2001) Exp. Opin. Emerging Drugs, 6(2): 187–98.*
Verma, et al. (1997) Nature, 389: 239–42.*
Eck, et al. (1996) Goodman & Gilman's The Pharmacological Basis of Therapeutics, 9th Ed., McGraw–Hll, New York, NY., pp. 77–101.*
Cho, et al. (2002) Yonsei Medical Journal, 43(6): 722–28.*
Hughes (2004) J. Surg. Oncol., 85: 28–35.*
Accession No. Al702982 of the EST database, published Dec. 18, 1999.*
Accession No.: Al339936 of the EST databases published Dec. 29, 1998.*

* cited by examiner

*Primary Examiner*—Dave Trong Nguyen
*Assistant Examiner*—Robert M. Kelly
(74) *Attorney, Agent, or Firm*—Anderson Kill & Olick, PC

(57) ABSTRACT

The present invention provides a human tumor suppressor protein having the amino acid sequence of SEQ ID NO: 2; a polynucleotide encoding the tumor suppressor protein; an expression vector containing the polynucleotide; a microorganism or animal cell transformed with the expression vector; a method for suppressing proliferation of a cancer cell which comprises introducing the expression vector into a cancer cell to induce apoptosis thereof; and a pharmaceutical composition for preventing or treating cancer which comprises a therapeutically effective amount of the polynucleotide and a pharmaceutically acceptable carrier.

5 Claims, 14 Drawing Sheets

← 0.6 kb

← β-actin

← 0.6 kb

← β-actin

HUMAN CERVICAL CANCER SUPPRESSOR PROTEIN, POLYNUCLEOTIDE ENCODING THE PROTEIN, CELL TRANSFORMED WITH THE POLYNUCLEOTIDE AND METHOD FOR SUPPRESSING PROLIFERATION OF CANCER CELL USING THE EXPRESSION VECTOR

This application is a national phase filing of the PCT application PCT/KR00/01406, which was filed on Dec. 4, 2000, which claims the benefit of priority to the Korean Patent Application No. 10-2000-0021897, which was filed on Apr. 25, 2000 in Korean Industrial Property Office, and is issued as a patent No. 10-0426455-0000 on Mar. 29, 2004 In the Republic of Korea.

FIELD OF THE INVENTION

The present invention relates to a human cervical cancer suppressor protein, a polynucleotide encoding said protein, an expression vector containing said polynucleotide, a cell transformed with said expression vector, a method for suppressing proliferation of cancer cells using said expression vector and a pharmaceutical composition for preventing or treating cancer comprising said polynucleotide.

BACKGROUND OF THE INVENTION

A tumor suppressor protein inhibits the transformation of a normal cell to a cancer cell and, therefore, loss of its activity, e.g., mutation, may contribute to the malignant transformation of a normal cell (Weinberg R A, *Science*, 254, 1138–1146 (1991); and Klein G., *FASEB J*, 7,821–825 (1993)).

Over twenty tumor suppressor genes and cancer-predisposition syndromes caused by mutation thereof have been reported (Haber D A et al., *Lancet*, 351, 1–8 (1998)). Among these, alterations of the coding sequences of the p53 tumor suppressor gene have been found to be responsible for most of the human cancers of genetical origin (Weinberg R A, vide supra; Klein G., vide supra; and Bishop J M, *Cell*, 64, 235–248 (1991)). However, only a small portion, i.e., 2 to 11%, of cervical cancer tissues exhibit p53 mutation (Crook T et al., *Lancet*, 339, 1070–1073 (1992); and Busby-Earle RMC et al. (Br. *J. Cancer*, 69, 732–737 (1994)) have suggested the existence of other tumor suppressor genes in case of cervical cancer. Therefore, there has existed a need to identify a gene which suppresses cervical cancer.

SUMMARY OF THE INVENTION

Accordingly, it is an object of the present invention to provide a tumor suppressor protein, a polynucleotide encoding the protein, an expression vector containing the polynucleotide and a cell transformed with the expression vector.

Another object of the present invention is to provide a method for suppressing proliferation of cancer cells using the expression vector.

A further object of the present invention is to provide a pharmaceutical composition for preventing or treating cancer comprising the polynucleotide.

In accordance with one aspect of the present invention, there is provided a tumor suppressor protein isolated from *Homo sapiens* which has the amino acid sequence of SEQ ID NO: 2.

BRIEF DESCRIPTION OF THE DRAWINGS

The above objects and features of the present invention will become apparent from the following description of the preferred embodiments taken in conjunction with the accompanying drawings, in which.

DETAILED DESCRIPTION OF THE INVENTION

Figure 1:
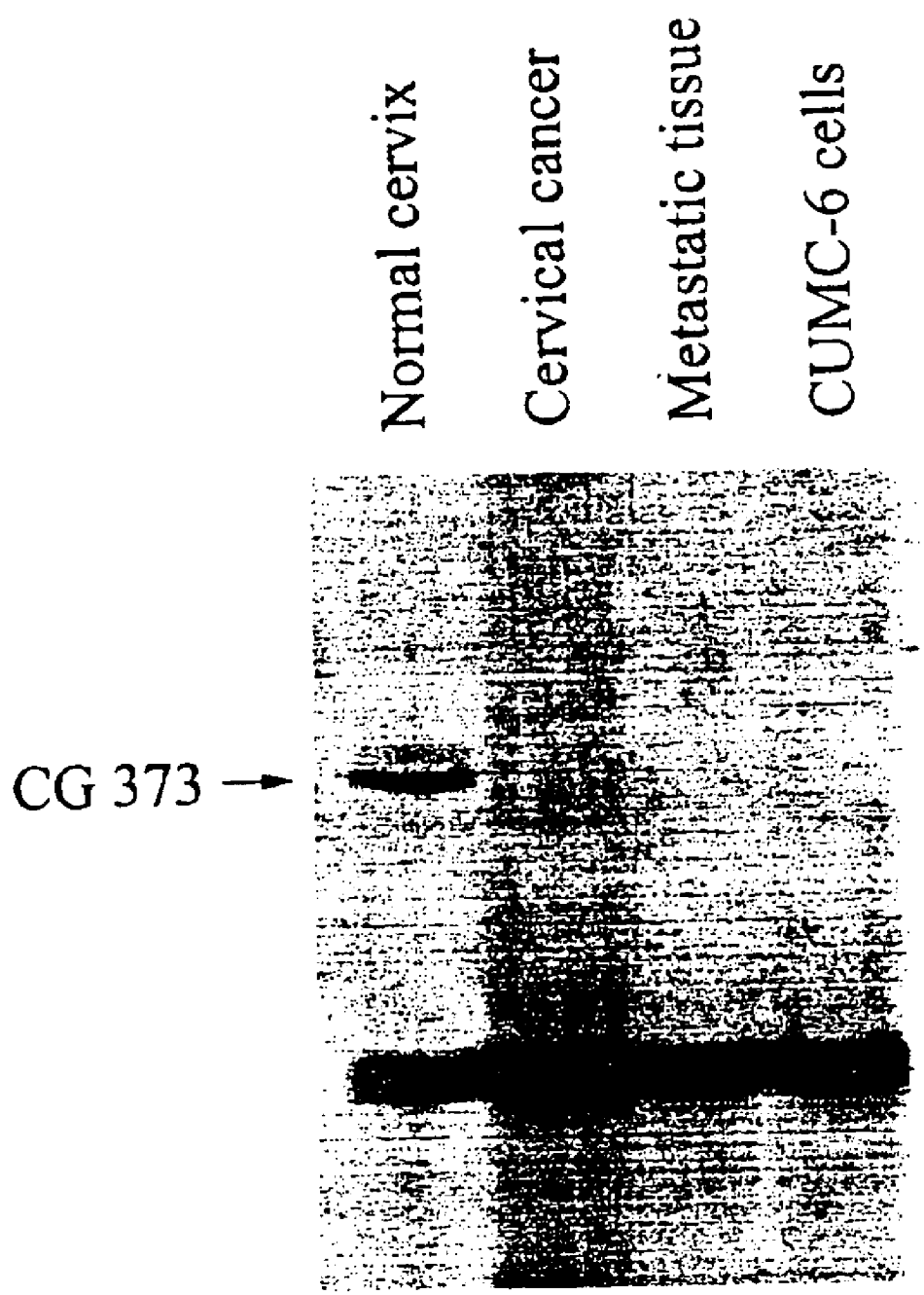
FIG. 1 is the differential display results of normal exocervical tissue, cervical cancer tissue, metastatic tissue and cervical cancer cell line CUMC-6.

The tumor suppressor protein of the present invention, i.e., human cervical cancer suppressor 1 protein (hereinafter "HCCS-1 protein"), has the amino acid sequence of SEQ ID NO: 2 and the molecular weight of about 9 kDa. However, various substitution, addition and/or deletion of the amino acid residues of the protein may be performed without adversely affecting the protein's function. Further, a portion of the protein may be used when a specific purpose is to be fulfilled. The term "the tumor suppressor protein of the present invention" used herein includes these modified amino acids and fragments thereof. Therefore, the present invention includes, in its scope, a polypeptide having substantially the same amino acid sequence as the HCCS-1 protein having the amino acid sequence of SEQ ID NO: 2 and a fragment thereof. As used herein, "substantially the same polypeptide" refers to a polypeptide whose amino acid sequence shows preferably 80% or more, more preferably 90% or more, most preferably 95% or more homology to the amino acid sequence of SEQ ID NO: 2.

The HCCS-1 protein of the present invention may be encoded by a polynucleotide comprising a nucleotide sequence deduced from the amino acid sequence of the HCCS-1 protein according to the genetic code (hereinafter "HCCS-1 gene"). It is known that several different codons encoding a same amino acid may exist due to the codon degeneracy, and, therefore, the HCCS-1 gene of the present invention may include various nucleotide sequences deduced from the amino acid sequence of the HCCS-1 protein. A preferred HCCS-1 gene has the nucleotide sequence of SEQ ID NO: 1, which is 555-bp long and contains an open reading frame of 79 amino acid residues. The nucleotide sequence of SEQ ID NO: 1 was registered at GenBank as accession no. AF249277 on Mar. 24, 2000.

The HCCS-1 gene, or the protein, of the present invention can be obtained from human tissue or synthesized using a conventional DNA or peptide synthesis method. Further, the gene thus prepared may be inserted into a conventional vector to obtain an expression vector, which may, in turn, be introduced into a suitable host, e.g., a microorganism such as an E. coli or yeast, or an animal cell such as a mouse or human cell.

The transformed host may then be used in producing the inventive DNA or protein on a large scale. For example, E. coli JM109 is transformed with expression vector pCEV-LAC (Miki, T. et al., Gene, 83, 137–146 (1989)) containing the inventive HCCS-1 gene (designated HCCS-1/pCEV-LAC) to obtain an E. coli transformant designated JM109/HCCS1 which was deposited with Korean Collection for Type Cultures (Address: #52, Oun-dong, Yusong-ku, Taejon 305–333, Republic of Korea) on Apr. 10, 2000 under the accession number of KCTC 0768BP, in accordance with the terms of the Budapest Treaty on the International Recognition of the Deposit of Microorganism for the Purpose of Patent Procedure.

In preparing a vector, expression-control sequences, e.g., a promoter, terminator, self replication sequence and secretion signal, are suitably selected depending on the host cell used.

The HCCS-1 gene of the present invention is expressed in normal human tissues, e.g., normal cervical, placenta, kidney, liver, skeletal muscle, heart tissues, but not in cancer tissues, e.g., primary cervical cancer and metastatic common iliac lymph node tissues, and cancer cell lines, e.g., promyelocytic leukemia HL-60 cell, HeLa cervical cancer cell, chronic myelogenous leukemia K-562 cell, lymphoblastic leukemia MOLT-4 cell, Burkitt's lymphoma Raji cell, SW480 colon cancer cell, A549 lung cancer cell and G361 melanoma cell. In a normal tissue, most of its transcripts has a length of 0.6 kb although 1.6 or 1.0 kb transcript has been observed.

The inventive HCCS-1 protein thus expressed has an activity for inducing apoptosis of the cancer cell. Specially, the HCCS-1 protein of the present invention induces cytochrome c release from mitochondria to cytosol to reach DNA fragmentation. Further, the HCCS-1 gene of the present invention generates plasma membrane lipid changes, e.g., translocation of phosphatidylserine (PS) of the inner leaflet into the extracellular side, to commit irreversibly to cell death. Furthermore, the HCCS-1 gene of the present invention induces cells more sensitive to an apoptic pathway triggered by chemotherapeutic agent, e.g., adriamycin, or radiation, e.g., UVC. The HCCS-1 gene of the present invention induces down-regulation of a tumor-promoting protein, e.g., a mutant p53 tumor suppressor protein, Bcl-2 or c-Myc.

Such an apoptosis-inducing activity of the inventive HCCS-1 protein may be advantageously used in suppressing proliferation of a cancer cell. Therefore, the present invention provides a method for suppressing proliferation of a cancer cell comprising introducing an expression vector containing the inventive HCCS-1 gene into a cancer cell to induce apoptosis thereof. Any type of cancer cell may be used in the inventive method. Preferred are cervical, placenta, kidney, liver, skeletal muscle and heart cancer cells, and more preferred is a cervical cancer cell.

The present invention also includes within its scope a pharmaceutical composition for treating or preventing cancer which comprises the inventive tumor suppressor gene as an active ingredient and pharmaceutically acceptable carriers, excipients or other additives, if necessary. The pharmaceutical composition of the present invention is preferably formulated for administration by injection.

The pharmaceutical composition of the present invention is administered into a cancerous tissue of a subject in a conventional manner to induce apoptosis of the tissue. For example, the tumor suppressor gene of the present invention is encapsulated using a hydrophobized poly-L-lysine derivative in accordance with the method disclosed by Kim, J. S. et al.(J. Controlled Release, 53, 175–182(1998)) and the resulting encapsulated gene is injected into a cancerous tissue of a subject.

The amount of the tumor suppressor gene actually administered should be determined in light of various relevant factors including the condition to be treated, the chosen route of administration, the age and weight of the individual patient, and the severity of the patient's symptoms.

The following Examples are intended to further illustrate the present invention without limiting its scope.

EXAMPLE 1

Differential Display of mRNA (Step 1) Isolation of Total RNA

Normal exocervical tissue specimens were obtained from uterine myoma patients during hysterectomy, and untreated primary cervical cancer and metastatic common iliac lymph node tissue specimens were obtained during radical hysterectomy. The human cervical cancer cell line CUMC-6 (Kim J W et al., Gynecol Oncol, 62, 230–240 (1996)) was cultured in Waymouth M B 751/1 medium.

Total RNAs were extracted from the tissue specimens and cells using a commercial system (RNeasy total RNA kit, Qiagen Inc., Germany), and DNA contaminants were removed therefrom using Message clean kit (GenHunter Corp., Brookline, Mass.).

(Step 2) Differential Display

Differential display was conducted according to Liang et al. (Science, 257, 967–971 (1992); and Cancer Res., 52, 6966–6968 (1992)) with minor modifications as follows.

0.2 μg each of the total RNAs obtained in Step 1 was subjected to reverse transcription using primer $H-T_{11}A$ (SEQ ID NO: 3), as an anchored oligo-dT primer (RNAimage kit, GenHunter), followed by polymerase chain reaction (PCR) using the same anchored primer and the arbitrary 5' 13 mer (RNAimage primer set 1, H-AP 1–40) in the presence of 0.5 mM [$\alpha$-$^{35}$S]-labeled dATP (1200 Ci/mmol). The PCR thermal cycle was repeated 40 times, each cycle being composed of: 95° C. for 40 sec., 40° C. for 2 min. and 72° C. for 40 sec., and finally the reaction was carried out at 72° C. for 5 min. The PCR product thus obtained was subjected to electrophoresis in 6% polyacrylamide sequencing gels, followed by autoradiography.

FIG. 1 shows the differential display results of normal exocervical tissue, cervical cancer tissue, metastatic tissue and cervical cancer cell line CUMC-6 using the anchored oligo-dT primer and the arbitrary 5' 13 mer H-AP 37 (SEQ ID NO: 4) wherein the arrow indicates a 193 bp fragment, designated CG373, expressed uniquely in the normal exocervial tissue. This result suggests that fragment CG373 is a tumor suppressor gene candidate.

The band of fragment CG373 was excised from the dried sequencing gel and boiled in water for 15 min. to elute fragment CG373. The fragment CG373 was subjected to PCR using the same conditions except that [$\alpha$-$^{35}$S]-labeled dATP and 20 μM dNTPs were omitted. The amplified fragment CG373 was cloned into the pGEM-T Easy vector using the TA Cloning System (Promega, USA) and its nucleotide sequence was determined using the Sequenase Version 2.0 DNA Sequencing System (United States Biochemical Co., USA) to obtain the nucleotide sequence of SEQ ID NO: 5. Comparative analysis of the nucleotide sequence of fragment CG373 with GenBank database was conducted using BLAST and FASTA programs and the result showed that this fragment has little sequence similarity to any nucleotide sequence registered in the GenBank database.

EXAMPLE 2 cDNA Library Screening

A bacteriophage λgt11 human lung embryonic fibroblast cDNA library (generously provided by Prof. I Y Chung at Hanyang University, Seoul, Korea) was screened by plaque hybridization with $^{32}$P-labeled random-primed CG373 cDNA probe (Sambrook, J. et la., *Molecular Cloning: A laboratory manual,* New York: Cold Spring Harbor Laboratory (1989)) to obtain a full-length cDNA clone (designated HCCS-1). The nucleotide sequence of the full-length HCCS-1 cDNA clone was determined.

The full-length HCCS-1 cDNA clone contains a 555 bp insert having the nucleotide sequence of SEQ ID NO: 1 and a full open reading frame encoding a polypeptide consisting of 79 amino acid residues (SEQ ID NO: 2) with an approximate molecular weight of 9 kDa. The nucleotide sequence of full-length HCCS-1 cDNA clone was registered at GenBank as accession no. AF249277 on Mar. 24, 2000.

The full-length HCCS-1 cDNA was inserted in vector pCEV-LAC (Miki, T. et al., *Gene,* 83, 137–146 (1989)) to obtain the recombinant vector HCCS-1/pCEV-LAC and *E. coli* JM109 was transformed with the recombinant vector HCCS-1/pCEV-LAC to obtain the transformed *E. coli* designated JM109/HCCS1 which was deposited with Korean Collection for Type Cultures (Address: #52, Oun-dong, Yusong-ku, Taejon 305–333, Republic of Korea) on Apr. 10, 2000 under the accession number of KCTC 0768BP.

In order to confirm the HCCS-1 protein, the full-length HCCS-1 cDNA was inserted at BamHI and SalI sites of the prokaryotic expression vector pGEX4T-1 (Amersham Pharmacia, USA). The resulting recombinant vector HCCS-1/pGEX4T-1 was transformed into *E. coli* BL21. The resulting transformant was cultured in LB media and the expression of the HCCS-1 gene was induced by adding isopropylthio-β-D-galactoside (IPTG) thereto and reacting the mixture at 37° C. for 3 hours. Protein samples were obtained from the culture samples taken before and after the induction and subjected to SDS-PAGE according to Sambrook et al.(vide supra).

Figure 2:
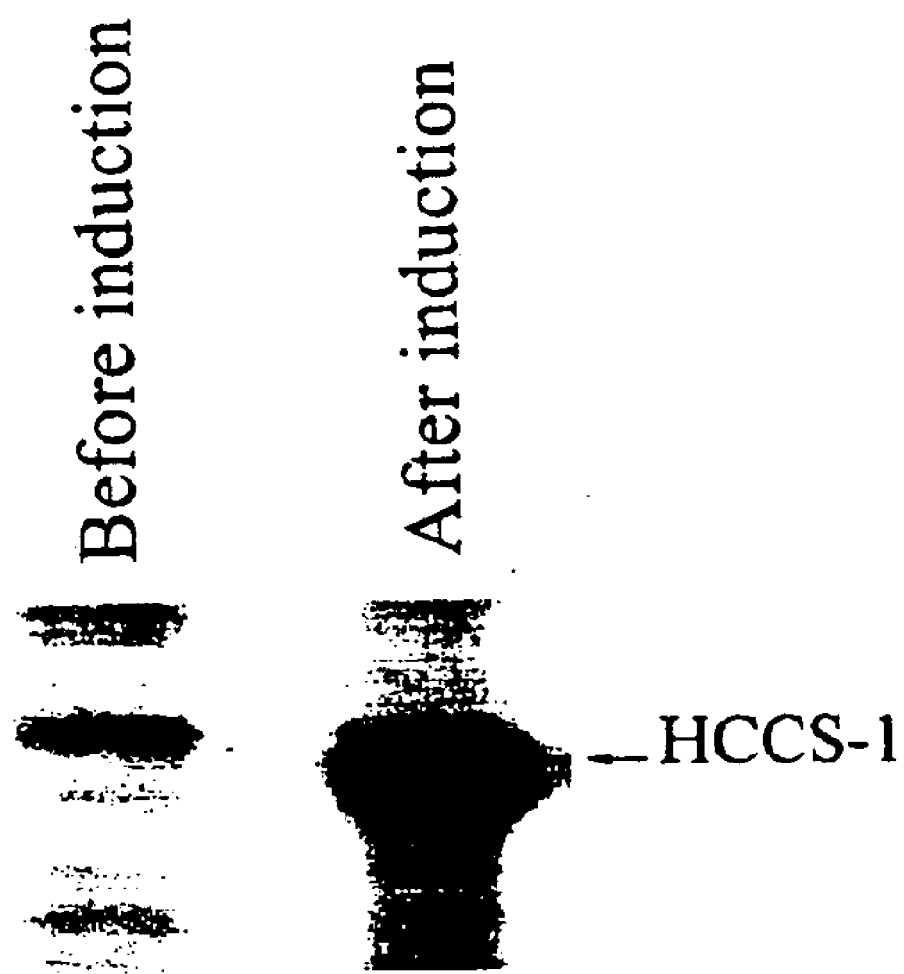
FIG. 2 is the SDS-PAGE analysis result of protein samples of the *E. coli* transformed with HCCS-1 gene before and after induction.

FIG. 2 shows the SDS-PAGE analysis result of the protein samples of the *E. coli* transformed with HCCS-1 gene before and after the induction. As can be seen from FIG. 2, a 35 kDa protein was expressed after the induction, the protein being composed of HCCS-1 protein fused with 26 kDa protein derived from pGEX4T-1. This result suggests that HCCS-1 protein has a relative molecular mass of approximately 9 kDa.

EXAMPLE 3

Northern Blot Analysis

To determine the expression level of HCCS-1 gene in various normal tissues, cancer tissues and cancer cell lines, the northern blot analysis was conducted as follows.

Total RNAs were prepared from normal exocervical tissue, primary cervical cancer and metastatic common iliac lymph node tissue; and human cervical cancer cell lines CUMC-6 and HeLa (ATCC CCL-2) by repeating the procedure of Step 1 of Example 1. 20 μg each of the total RNAs were denatured and then electrophoresed through 1% formaldehyde agarose gel and transferred to nylon membranes (Boehringer-Mannheim, Germany). The blots were hybridized overnight at 42° C. with $^{32}$P-labeled random-primed HCCS-1 cDNA probe which was prepared using a rediprime II random prime labeling system (Amersham, England). The northern blot analysis results were consistently repeated two times, as quantified by densitometry and the same blots were hybridized with a β-actin probe to confirm mRNA integrity.

Using normal human 12 multiple-tissues (Clontech) and human cancer cell lines (Clontech), northern blot analyses were also carried out as recommended by the supplier.

Figure 3A:
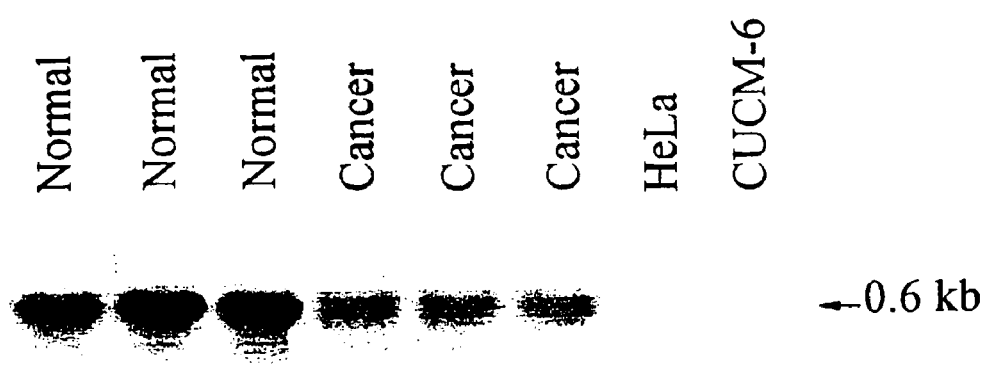
FIG. 3A is the northern blot analysis results showing the expression level of HCCS-1 gene in normal cervical tissues, primary cervical cancer tissues and cervical cancer cell lines HeLa and CUMC-6.
Figure 3B:
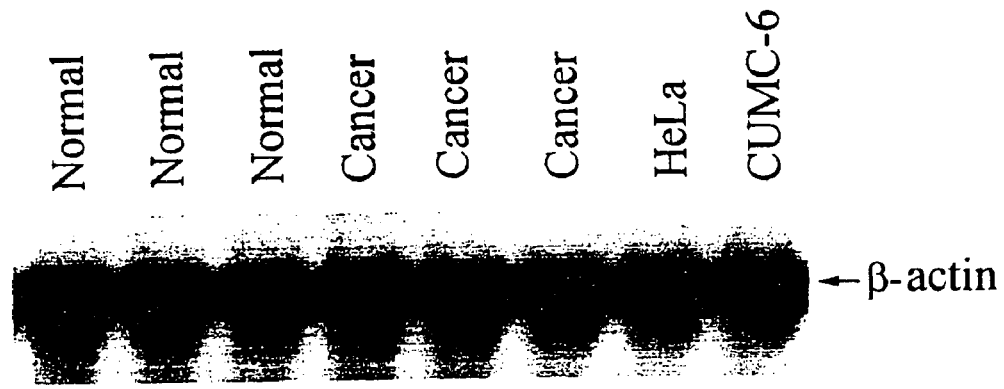
FIG. 3B is the same blot hybridized with a β-actin probe.

FIG. 3A shows the northern blot analysis results of normal cervical tissues, primary cervical cancer tissues and cervical cancer cell lines HeLa and CUMC-6 using the HCCS-1 cDNA probe; and FIG. 3B, the same blot hybridized with a β-actin probe. As can be seen from FIGS. 3A and 3B, the expression level of HCCS-1 gene was elevated in all normal cervical tissues but nearly absent in the cervical cancer tissues and the cervical cancer cell lines.

Figure 4A:
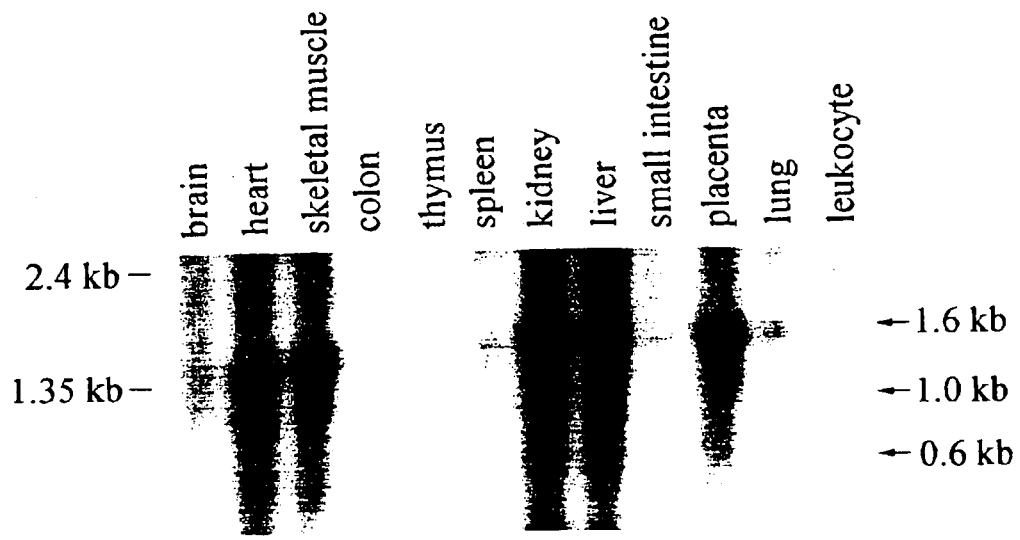
FIG. 4A is the northern blot analysis results showing the expression level of HCCS-1 gene in normal human tissues.
Figure 4B:
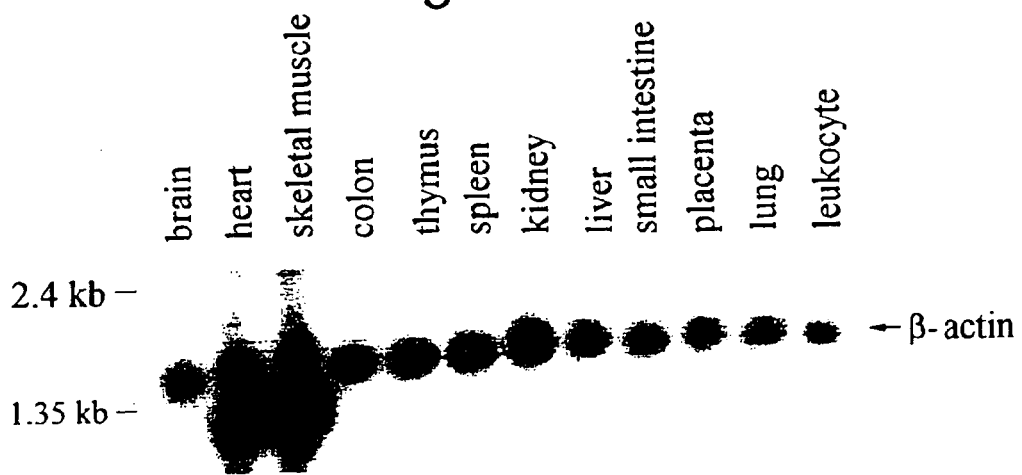
FIG. 4B is the same blot hybridized with a β-actin probe.

FIG. 4A shows the northern blot analysis results of normal human tissues, i.e., brain, heart, skeletal muscle, colon, thymus, spleen, kidney, liver, small intestine, placenta, lung and peripheral blood leukocyte using HCCS-1 cDNA probe; and FIG. 4B, the same blot hybridized with a β-actin probe. As can be seen from FIGS. 4A and 4B, a dominant HCCS-1 mRNA transcript of approximately 1.6 kb was also overexpressed in normal placenta, kidney, liver, skeletal muscle and heart, and other tissues that demonstrated low levels of expression include, in descending order, the lung, spleen, peripheral blood leukocyte and colon tissues. In addition, transcripts of approximately 1.0 and 0.6 kb were identified in placenta, kidney, liver, skeletal muscle and heart tissues.

Figure 5A:
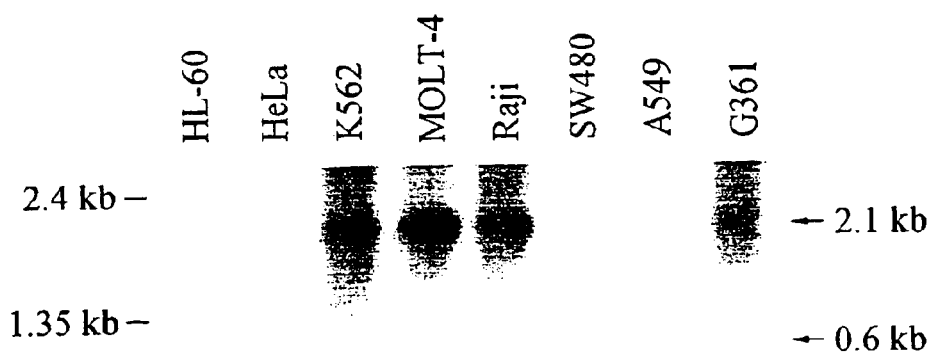
FIG. 5A is the northern blot analysis results showing the expression level of HCCS-1 gene in human leukemia and lymphoma cell lines.
Figure 5B:
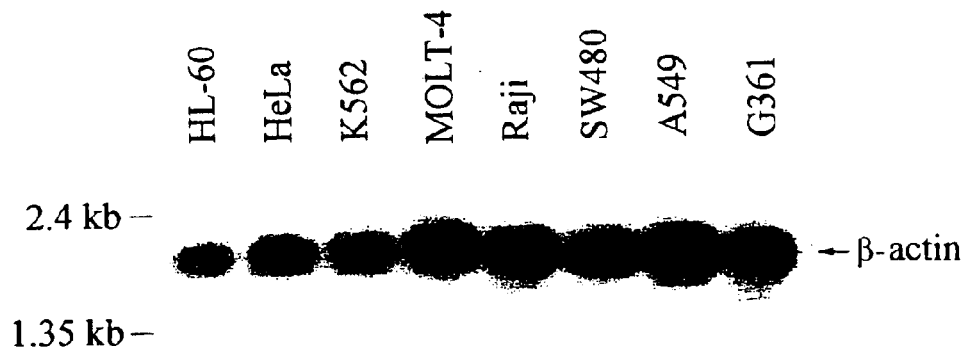
FIG. 5B is the same blot hybridized with a β-actin probe.

FIG. 5A shows the northern blot analysis results of human leukemia and lymphoma cell lines, i.e., promyelocytic leukemia HL-60 cell, HeLa cervical cancer cell, chronic myelogenous leukemia K-562 cell, lymphoblastic leukemia MOLT-4 cell, Burkitt's lymphoma Raji cell, SW480 colon cancer cell, A549 lung cancer cell and G361 melanoma cell using the HCCS-1 cDNA probe; and FIG. 5B, the same blot hybridized with a β-actin probe. As can be seen from FIGS. 5A and 5B, 0.6, 1.0 and 1.6 kb HCCS-1 transcripts were not detected in the human leukemia and lymphoma cell lines.

EXAMPLE 4

Preparation of HeLa Cell Transfected with Human HCCS-1 Gene (Step 1) Construction of Expression Vector The recombinant vector HCCS-1/pCEV-LAC prepared in Example 2 was cleaved with SalI to obtain a fragment containing 555 bp full length HCCS-1 cDNA. Then, the SalI fragment was inserted into SalI site of eukaryotic expression vector pCEV-27 (Miki, T. et al., *Gene,* 83, 137–146 (1989)) to obtain expression vector HCCS-1/pCEV-27.

(Step 2) Transfection

The expression vector HCCS-1/pCEV-27 obtained in Step 1 was introduced into HeLa cervical cancer cells (ATCC CCL-2) using lipofectamine (Gibco BRL), and then the resulting HeLa cells transfected with the expression vector HCCS-1/pCEV-27 was selected in media supplemented with 0.6 mg/ml G418 (Gibco). Another population of HeLa cells containing pcDNA3 alone was prepared as a control.

The transfected HeLa cells were cloned and screened for the over-expression of HCCS-1 gene. Total RNAs were obtained from the transfected HeLa cells by repeating the procedure of Step 1 of Example 1, electrophoresed and transferred to nylon membranes. The blots were hybridized with $^{32}$P-labeled random-primed HCCS-1 cDNA probe.

Figure 6A:
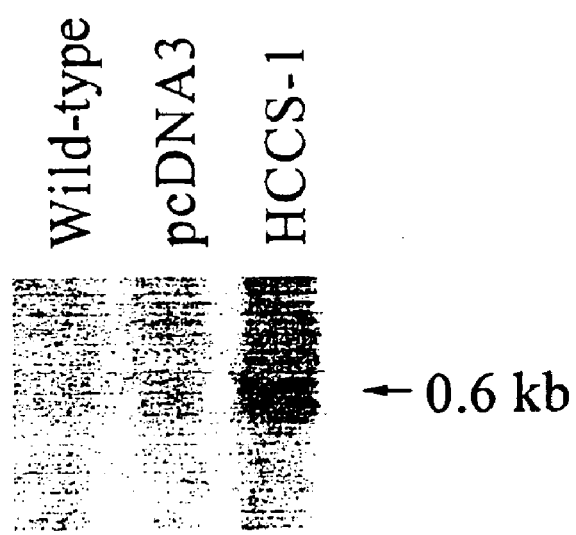
FIG. 6A is the northern blot analysis result showing the expression level of HCCS-1 gene in the HeLa cells transfected with HCCS-1 gene, HeLa cells transfected with vector pcDNA3 alone and parental wild-type cells.
Figure 6B:
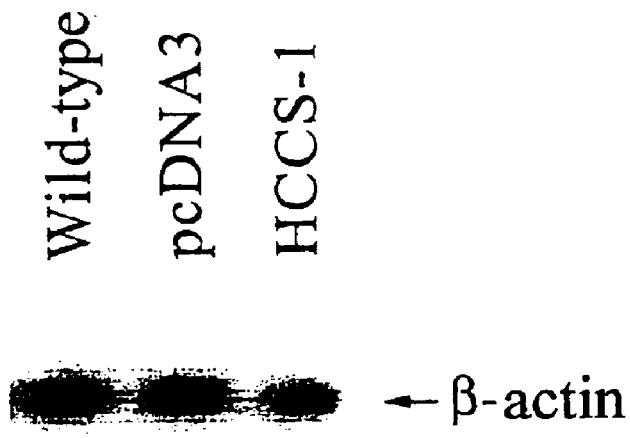
FIG. 6B is the result of the same blot using β-actin probe.

FIG. 6 shows the northern blot analysis results of the HeLa cells transfected with HCCS-1 gene (HCCS-1), HeLa cells transfected with vector pcDNA3 alone (pcDNA3) and parental wild-type HeLa cells, respectively. As can be seen from FIG. 6, a single 0.6 kb mRNA transcript, which is identical to that of the normal cervical tissues shown in Example 3, was expressed in HeLa cells transfected with HCCS-1 gene but not in the HeLa cells transfected with vector pcDNA3 alone and parental wild-type HeLa cells.

EXAMPLE 5

Growth Inhibition of Cancer Cell by HCCS-1 Gene

To examine the effect of HCCS-1 gene on cervical cancer cell growth, each of HeLa cells transfected with HCCS-1 gene obtained in Step 2 of Example 4, HeLa cells transfected with pcDNA3 alone and wild-type HeLa cells (in a cell number of 1×10$^5$) were cultured for 9 days. In three independent experiments, cells in triplicate flasks were detached using trypsin and viable cells were counted on days 0, 1, 3, 5, 7 and 9, respectively, using trypan blue dye exclusion (Freshney, I. R., Culture of animal cells, 2nd Ed. A. R. Liss, New York (1987)). The data were represented by the mean ±S.D. of triplicate determinations.

Figure 7:
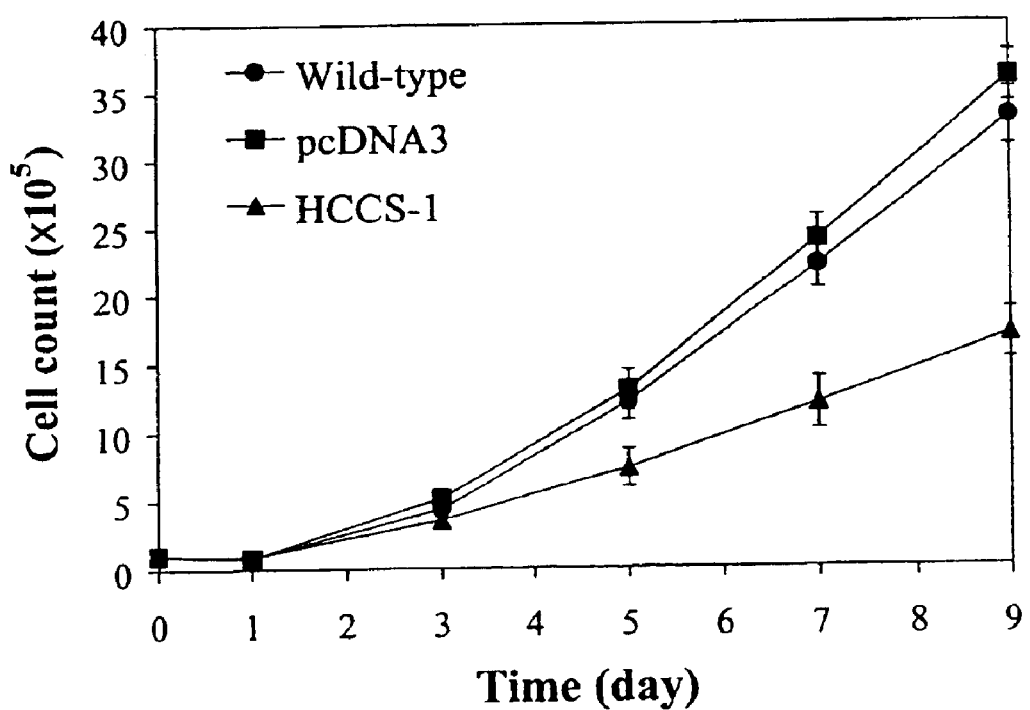
FIG. 7 is the growth curves of HeLa cells transfected with HCCS-1 gene, HeLa cells transfected with pcDNA3 alone and parental wild-type cells.

FIG. 7 shows the growth curves of HeLa cells transfected with HCCS-1 gene (HCCS-1), HeLa cells transfected with pcDNA3 alone (pcDNA3) and parental wild-type cells. As can be seen from FIG. 7, the death rate of HeLa cell transfected HCCS-1 gene increased compared to those of cells transfected with pcDNA3 alone or wild-type HeLa cells. About 50% of HeLa cells transfected with HCCS-1 gene remained viable at 9 days when compared with wild-type HeLa cells. This result suggests that HCCS-1 gene inhibits growth of HeLa cervical cancer cells.

EXAMPLE 6

Apoptosis-Inducing Activity of HCCS-1 Gene

In order to examine whether the HCCS-1 gene has an apoptosis-inducing activity, DNA fragmentation, cytoplasmic translocation of cytochrome c, membrane PS change and chemotherapeutic agent-triggered apoptosis of HeLa cell transfected with HCCS-1 gene were examined as follow.

(1) DNA Fragmentation Analysis

HeLa cells transfected with HCCS-1 gene obtained in Step 2 of Example 4, HeLa cells transfected with pcDNA3 alone, and parental wild-type HeLa cells were cultured in Waymouth MB 751/1 medium for 3, 5 or 7 days, and then further cultured for 1 day in serum-free medium. The cells were collected and lysed overnight at 48° C. in a lysis buffer (10 mM Tris-HCl, pH 7.4, 10 mM EDTA, 10 mM NaCl, and 0.5% SDS) containing 100 μg/ml of proteinase K. A ⅕ volume of 5 M NaCl and an equal volume of isoamyl alcohol were added thereto to precipitate DNA. The DNA pellet was redissolved in TE buffer (10 mM Tris-HCl, pH 7.8, 1 mM EDTA) and treated with 0.1 mg/ml of RNase A at 37° C. for 4 hours. 5 μg of DNA were electrophoresed on a 1% agarose gel, stained with ethidium bromide, and visualized under UV light.

Figure 8:
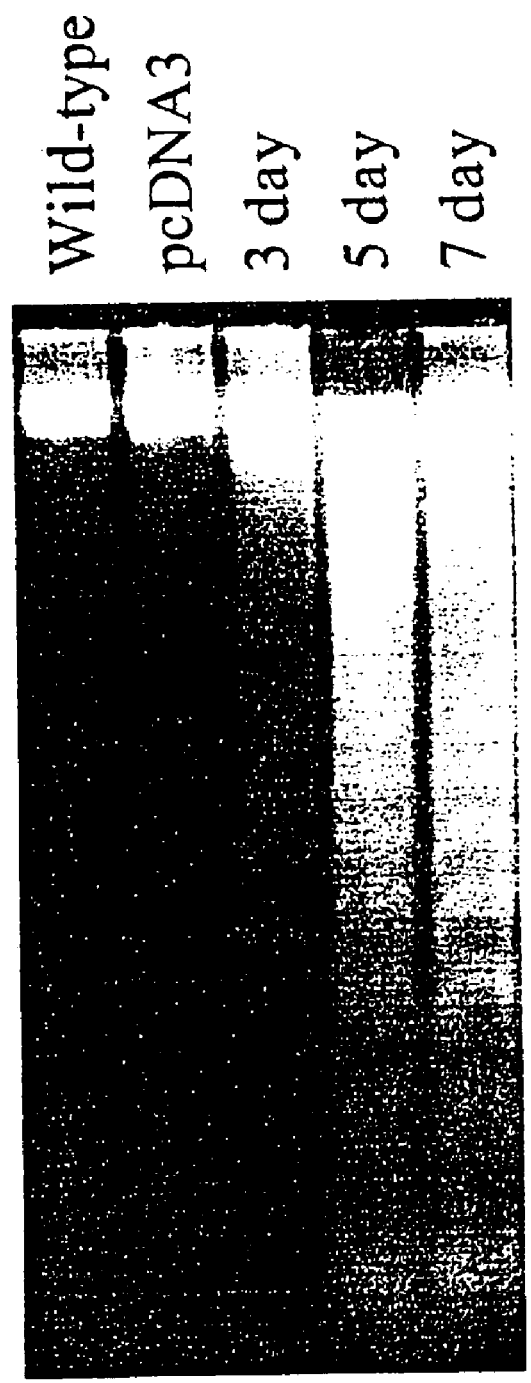
FIG. 8 is the DNA fragmentation analysis results of the HeLa cell transfected with HCCS-1 gene, HeLa cell transfected with pcDNA3 and the parental wild-type cell.

FIG. 8 shows the DNA fragmentation analysis results of the HeLa cell transfected with HCCS-1 gene at days 3, 5 and 7 (day 3, day 5 and day 7, respectively), HeLa cell transfected with pcDNA3 (pcDNA3) at day 7 and the parental wild-type HeLa cell at day 7. As can be seen from FIG. 8, during the course of the cell death in the serum-free medium, the fragmentation of DNA into oligonucleosomal ladders was obvious in HeLa cells transfected with HCCS-1 gene compared with parental wild-type cells in a time-dependent manner, which suggests that the HCCS-1 gene induces apoptosis in cervical cancer cells.

(2) Cytoplasmic Translocation of Cytochrome c

To examine cytoplasmic translocation of cytochrome c in the transfected cells, the cytochrome c content of the subcellular fraction was determined according to Akao Y et al.(*Cancer Res,* 54, 2468–71 (1994)) as follows.

(Step 1) Subcellular Fractionation

The HeLa cells transfected with HCCS-1 gene obtained in Step 2 of Example 4 were washed with PBS and suspended in hypotonic solution (10 mM 4-(2-hydroxylethyl)-1-piperazineethanesulfonic acid, 10 mM MgCl$_2$ and 42 mM KCl) on ice for 5 min. Cells were passed through a 30-gauge needle and centrifuged at 600 g for 10 min. to collect crude nuclei. The supernatant was centrifuged at 10,000 g for 10 min. to obtain a supernatant, which was further centrifuged at 100,000 g for 90 min. The resulting pellet and supernatant were used as light membrane (mitochondrial fraction) and cytoplasmic fractions, respectively.

(Step 2) Western Blot

To measure the cytochrome c contents of cytosolic and mitochondrial fractions, western blot was conducted as follows.

The cytosolic and mitochondrial fractions obtained in Step 1 were electrophoresed on 10% SDS-PAGE and then electroblotted onto nitrocellulose membrane. The membrane was incubated with 5% non-fat dry milk in tris-buffered saline (TBS; 10 mM Tris-HCl, pH 7.5 and 150 mM NaCl) for 1 hour and incubated with primary antibodies, i.e., monoclonal mouse anti-cytochrome C (PharMingen, USA), at 4° C. for 16 hours. The resulting membrane was washed and then incubated with a blocking solution containing 1:1,000 dilution of secondary antibodies, i.e., horseradish peroxidase-conjugated secondary goat anti-mouse or goat anti-rabbit immunoglobulins (Jackson ImmunoResearch) at room temperature. Proteins were revealed by an ECL-Western blot detection kit (Amersham, Buckinghamshire, UK).

Figure 9:
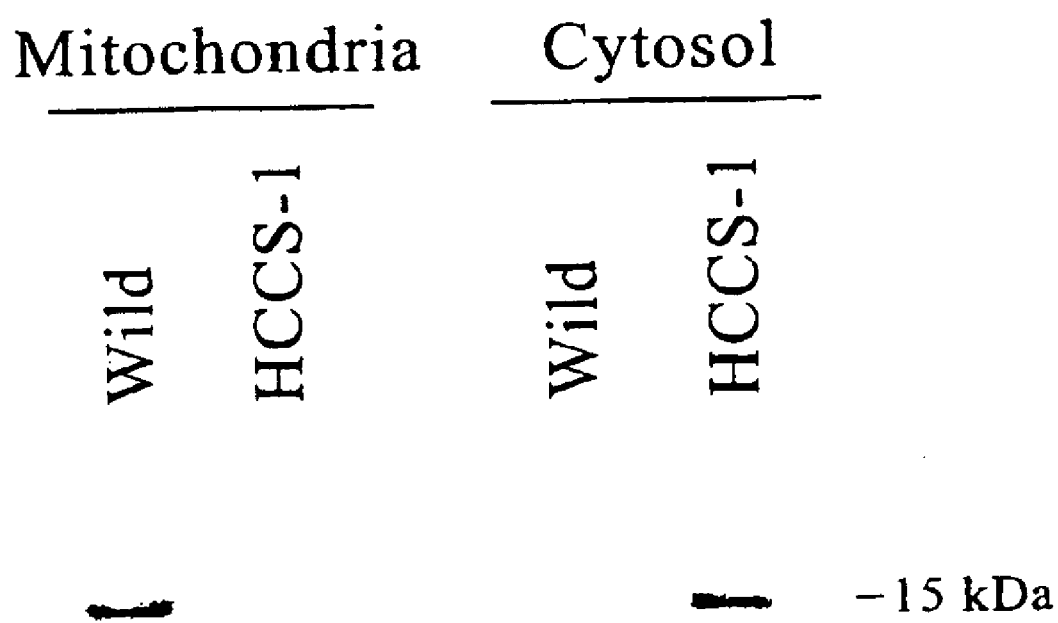
FIG. 9 is the western blot analysis results showing the cytochrome c contents of cytoplasmic and mitochondrial fractions.

FIG. 9 shows the western blot analysis results of mitochondrial and cytoplasmic fractions of HeLa cell transfected with HCCS-1 gene (HCCS-1) and parental wild-type HeLa cell (wild). As can be seen from FIG. 9, the cytochrome c of mitochondrial fraction was depleted while that of cytosolic fraction was increased in a concomitant manner in HeLa cells transfected with HCCS-1 gene. These results suggest that the HCCS-1 gene induces release of cytochrome c from mitochondria to cytosol.

(3) Membrane PS Change

To examine the plasma membrane PS translocation, the Flow cytometric analysis combined with annexin V/PI assay system (Vermes I et al., *J Immunol Methods.*, 184, 39–51 (1995)) was conducted as follows.

$1 \times 10^7$ HeLa cells transfected with HCCS-1 gene obtained in Step 2 of Example 4 were washed with cold PBS and diluted in 10 μl of 10× binding buffer (100 mM HEPES pH 7.4, 1.5 M NaCl, 50 mM KCl, 10 mM $MgCl_2$ and 18 mM $CaCl_2$). 1 μl of annexin V-conjugate and 10 μl of propidium iodide (PI) were added thereto as instructed by the producer of the apoptosis kit (TACSTM Annexin V-FITC, Trevigen, Inc., Gaithersburg, Md., USA). The resulting cell suspension was incubated at room temperature in the dark for 15 min., and 400 μl of 1× binding buffer was added thereto and then analyzed on a Coulter XL Epics Flow Cytometer (Coulter Corp., Miami, Fla.).

Figure 10A:
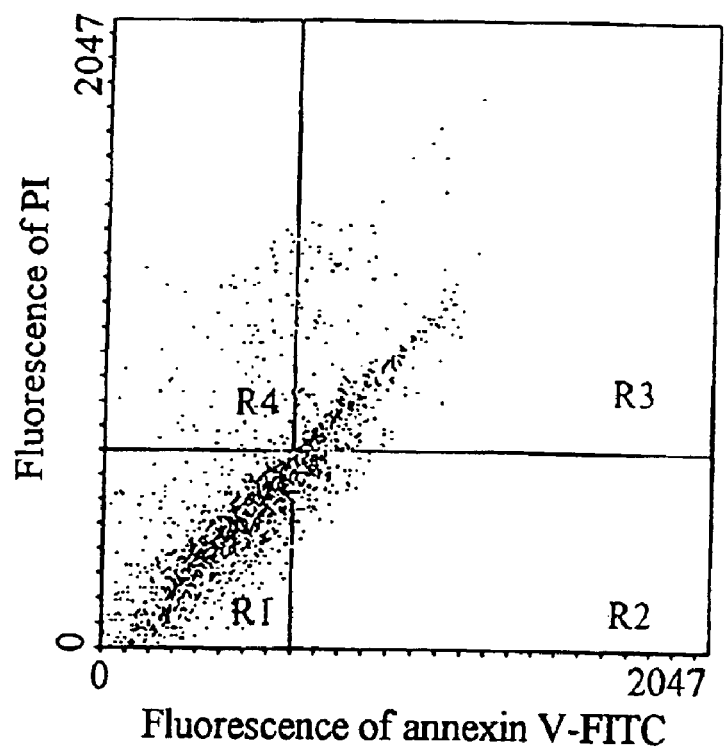
FIGS. 10A and 10B are the flow cytometric analysis results of HCCS-1-transfected HeLa cells and parental wild-type cells, respectively, stained with Annexin V-FITC and PI.
Figure 10B:
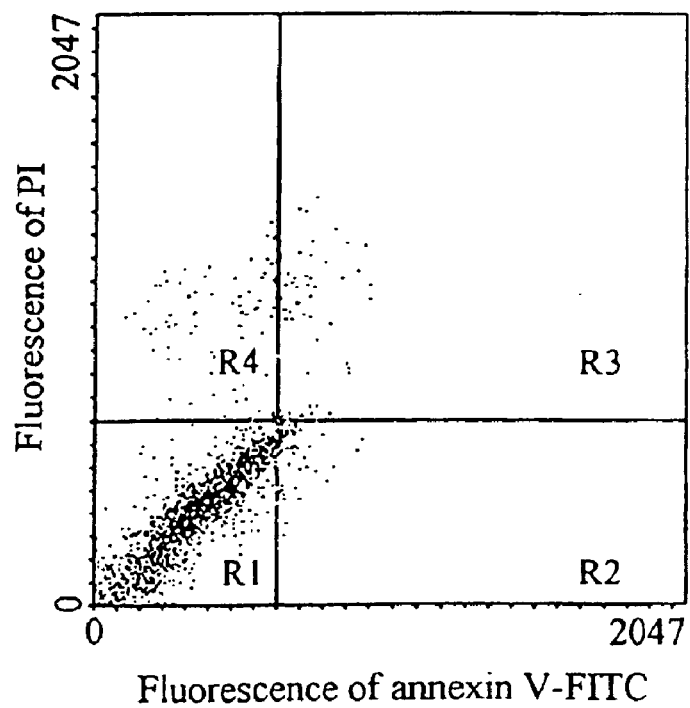

FIGS. 10A and 10B show the flow cytometric analysis results of HeLa cells transfected with HCCS-1 gene and parental wild-type cells, respectively, using Annexin V-FITC and PI. In FIGS. 10A and 10B, log green fluorescence (annexin V-FITC) versus log red fluorescence (PI) revealed four populations: negative cells for both fluorochromes (R1; lower left quadrant) which represent living target cells; annexin V-FITC-positive and PI-negative cells (R2; lower right quadrant) which characterize early apoptotic cells; positive cells for both fluorochromes (R3; upper right quadrant) which identify late stage apoptotic or necrotic cells and annexin V-FITC-negative and PI-positive cells (R4; upper left quadrant) which represent cells with permeabilized membranes only (Aubry J-P et al., *Cytometry*, 37, 197–204 (1999)), As can be seen from FIGS. 10A and 10B, there are viable (R1), early apoptotic (R2), and late apoptotic or necrotic (R3) cells, and 22% of total HeLa cells transfected with HCCS-1 gene were in the early apoptotic process whereas 2.2% of wild-type HeLa cells were. This result suggests that HCCS-1 gene induced apoptosis-associated plasma membrane lipid changes.

These annexin V/PI flow cytometry results were well correlated with cytochrome c release result of (2) in that HCCS-1 induced apoptosis in HeLa cervical cancer cells.

(4) Adriamycin or UVC-Triggered Apoptosis

To examine whether a drug or UV light triggers apoptosis of the cells transfected with HCCS-1 gene, the cell cycle kinetic analysis was conducted as described by Hedley, D. W.(in Flow Cytometry, DNA Analysis from Paraffin-embedded Blocks (eds Darzynkiewicz, Z. & Crissman, H. A.) 139 (Academic Press, San Diego, 1990)).

HeLa cells transfected with HCCS-1 gene obtained in Step 2 of Example 4 and parental wild-type cells were cultured until mid-log phase and incubated in Waymouth MB 752/1 medium containing 0.5% bovine calf serum for 36 hours to arrest the cell growth at $G_0/G_1$ phase. The cells were treated with adriamycin (0.1 and 2 μg/ml, respectively) or UVC (50 $J/m^2$) and then the cells were cultured in Waymouth MB 752/1 medium containing 0.5% bovine calf to resume the cell growth. After 24 hours, HeLa cells were harvested, treated with trypsin, and fixed in 70% ethanol.

50 μg/ml of PI staining solution (Sigma) and 100 units/ml of RNase A (Boerhinger Mannheim) were added to $2 \times 10^6$ of the fixed cells. After incubation for 1 hour, the cellular DNA content was determined by fluorescence analysis at 488 nm using a FACS Caliber (Becton Dickinson). A minimum of $1 \times 10^4$ cells per sample was analyzed with Modfit 5.2 software.

Figure 11A:
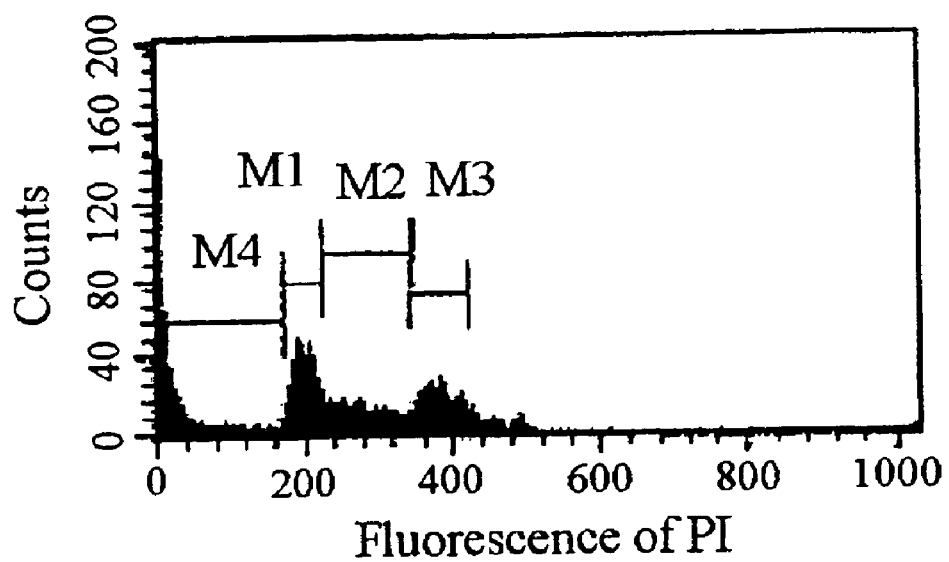
FIGS. 11A and 11B are the cell-cycle profiles of HeLa cells transfected with HCCS-1 gene and parental wild-type cells, respectively, without treatment of adriamycin or UVC.
Figure 11B:
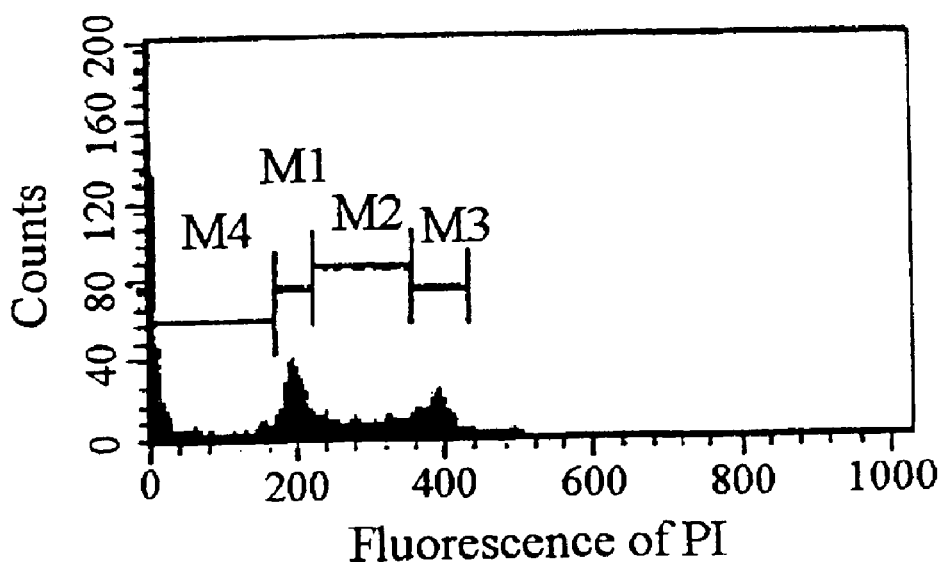
Figure 11C:
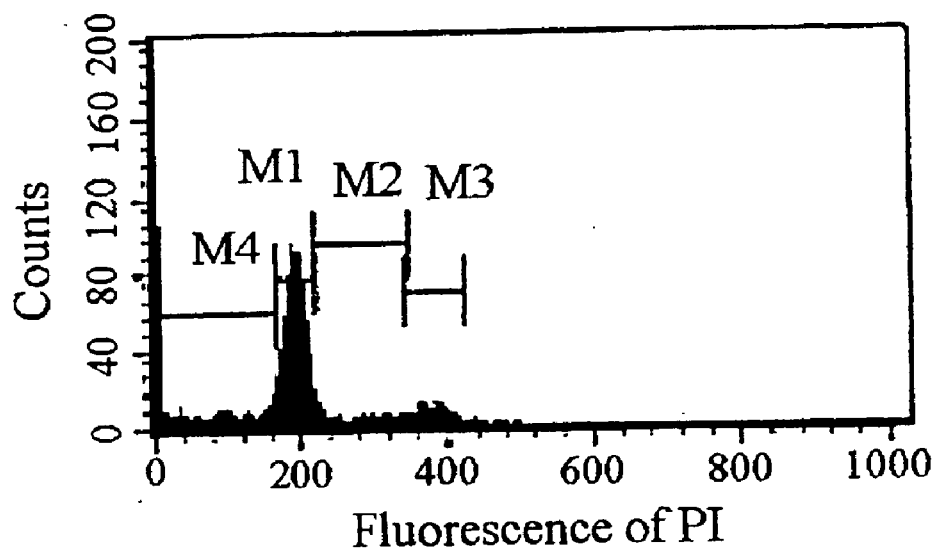
FIGS. 11C and 11D, after treatment of 0.1 μg/ml adriamycin.
Figure 11D:
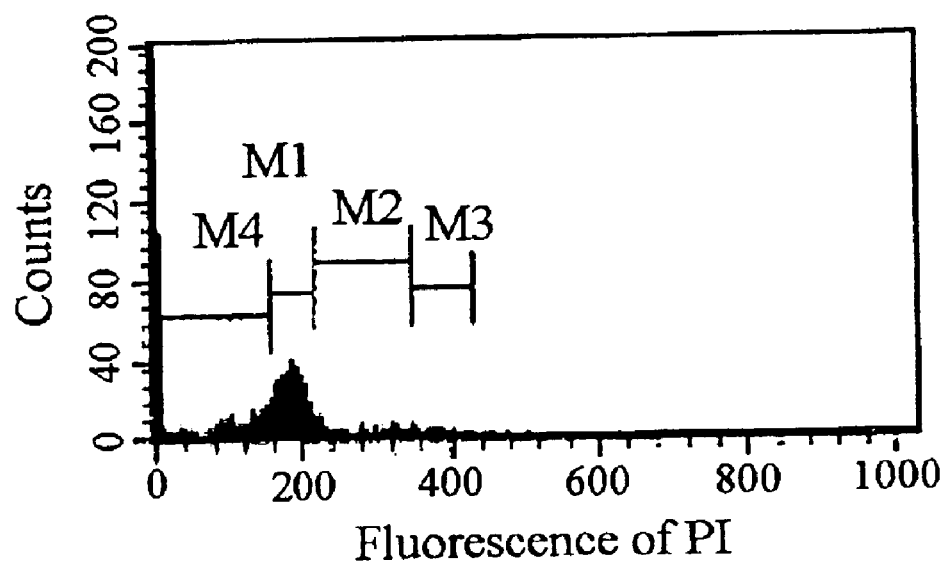
Figure 11E:
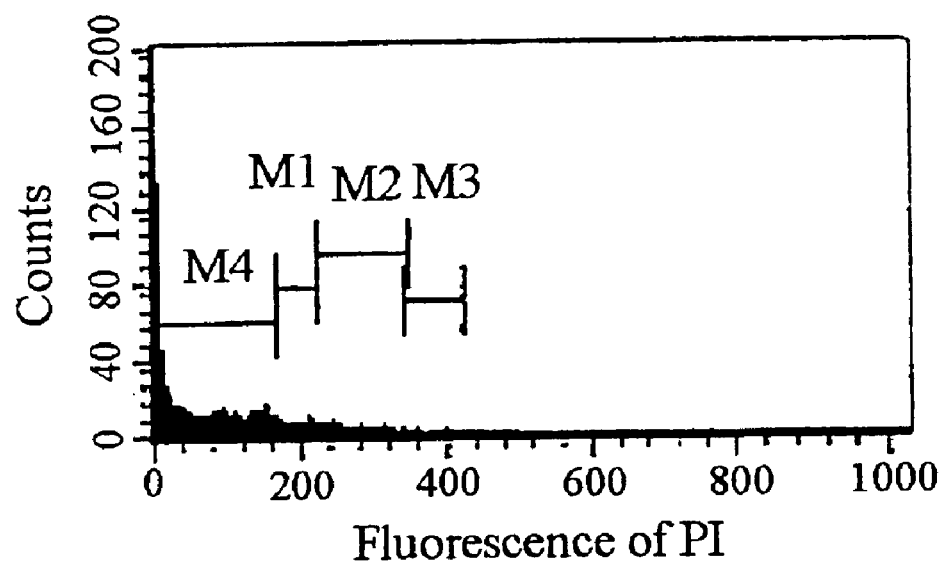
FIGS. 11E and 11F, after treatment of 2 μg/ml adriamycin.
Figure 11F:
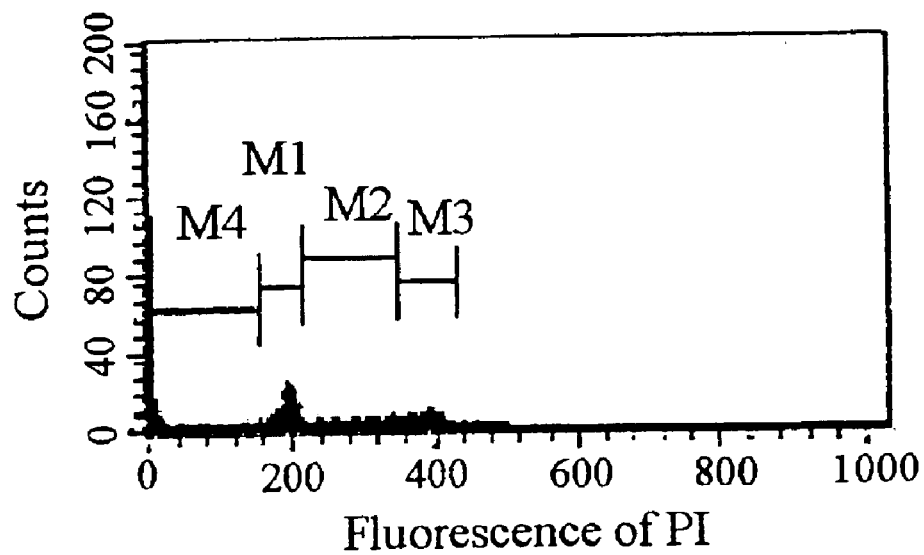
Figure 11G:
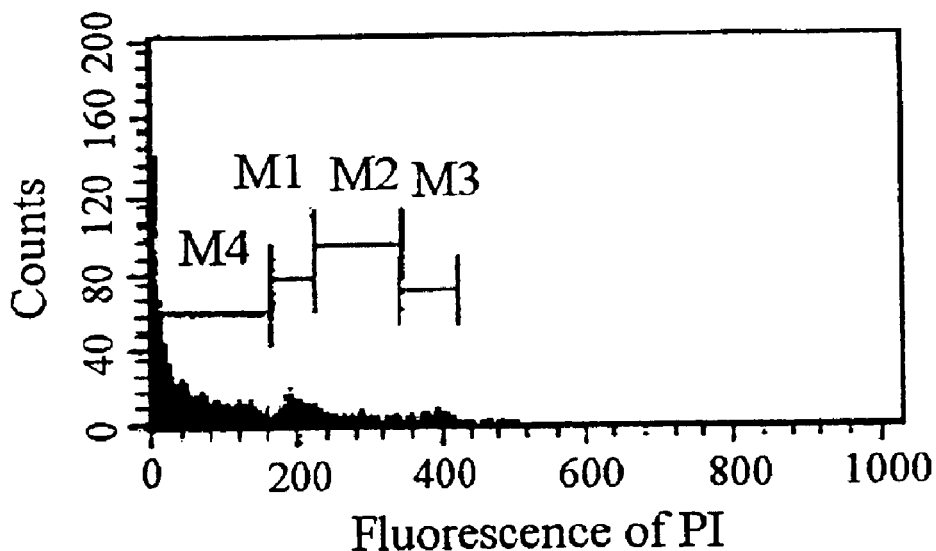
FIGS. 11G and 11H, after treatment of UVC.
Figure 11H:
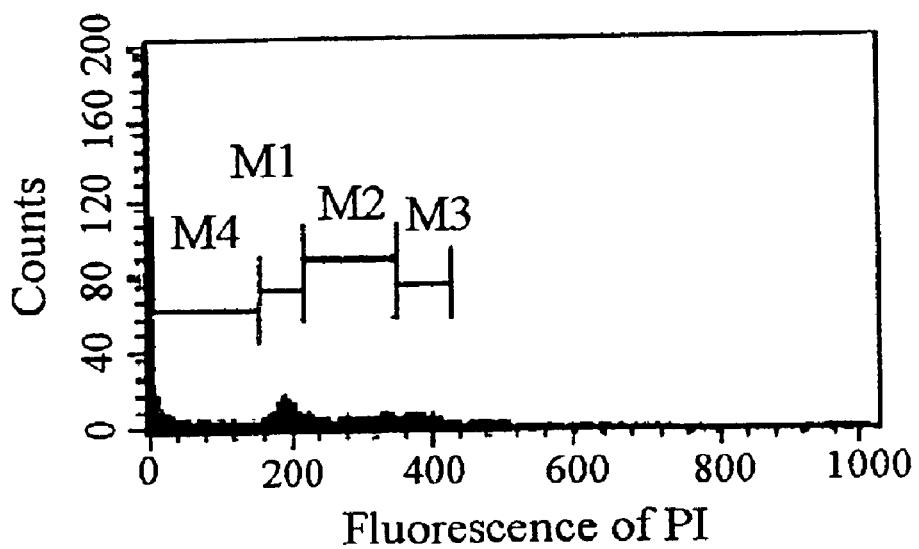

FIGS. 11A and 11B are the cell-cycle profiles of HeLa cells transfected with HCCS-1 gene and parental wild-type cells, respectively, without treatment of adriamycin or UVC; FIGS. 11C and 11D, after treatment of 0.1 μg/ml adriamycin; FIGS. 11E and 11F, after treatment of 2 μg/ml adriamycin; and FIGS. 11G and 11H, after treatment of UVC, wherein M1 represents $G_0/G_1$-phase; M2, S-phase; M3, $G_2$/M-phase; and M4, apoptotic sub $G_0/G_1$ phase. As can be seen from FIGS. 11A to 11H, adriamycin induced no significant differences in cell populations with respect to cell cycle progression between parental wild-type cells and HeLa cells transfected with HCCS-1 gene. In wild-type HeLa cells, few cells remained in apoptotic sub $G_0/G_1$-phase after treatment with adriamycin or UVC. In contrast, a considerable amount of HeLa cells transfected with HCCS-1 gene were still in the apoptotic sub $G_0/G_1$-phase. These results suggest that HCCS-1 gene induced cells more sensitive to drug or UV light-triggered apoptosis.

While the subject invention has been described and illustrated with reference to the preferred embodiments only, it may be apparent to those skilled in the art that various changes and modifications can be made therein without departing from the spirit and scope of the present invention which is defined in the appended claims.

What is claimed is:

1. A polynucleotide which encodes a tumor suppressor protein and comprises the nucleotide sequence of SEQ ID NO: 1.

2. An expression vector containing the polynucleotide of claim 1.

3. The expression vector of claim 2, which is vector HCCS-1/pCEVLAC.

4. An isolated cell comprising the expression vector of claim 2, the cell being a microorganism or animal cell.

5. The cell of claim 4, which is *Escherichia coli* JM109/HCCS1 (KCTC 0768BP).

* * * * *

SEQUENCE LISTING

<160> NUMBER OF SEQ ID NOS: 5

<210> SEQ ID NO 1
<211> LENGTH: 555
<212> TYPE: DNA
<213> ORGANISM: Homo sapiens
<220> FEATURE:
<221> NAME/KEY: CDS
<222> LOCATION: (283)..(522)

<400> SEQUENCE: 1

```
ggccattacc aatcgcgaaa cccgaatccc ggacctgcgc tgaggaggcg gttcatctgt      60
ggccagcggt gcttcgggac ccgcgctggg ggaaccctgg cgacggggcc tggccctgct     120
```

-continued

```
atatgcgggg gcctcggctg gagtgagcgg cgtggacgcc tctttcctcc ggctcttccc    180
ttgttgctgc gagagcgaga gggccgcggg cggcggaggc agcggggccg ggatggagga    240
cgttaactct aacgtgaacg cggaccagga ggctggagtg ca        atg gcg cga    291
                                                      Met Ala Arg
                                                       1
tct cgg ctc act gca acc tct gtc tcc cag gtt cag gaa aat ggc ttt      339
Ser Arg Leu Thr Ala Thr Ser Val Ser Gln Val Gln Glu Asn Gly Phe
      5              10                  15 gta aag aag ctt gag cct aaa tct ggc tgg atg act ttc cta gaa gtt      387
Val Lys Lys Leu Glu Pro Lys Ser Gly Trp Met Thr Phe Leu Glu Val
20              25                  30                  35 aca gga aag atc tgt gaa atg ctc ttc tgt cct gaa gca ata ctg ttg      435
Thr Gly Lys Ile Cys Glu Met Leu Phe Cys Pro Glu Ala Ile Leu Leu
                40                  45                  50 acc aga aag gac act cta tat tgt gaa acc ggc cta att ttt ctg act      483
Thr Arg Lys Asp Thr Leu Tyr Cys Glu Thr Gly Leu Ile Phe Leu Thr
                55                  60                  65 ctt acg aaa acg att gcc aac aca tac ttc tac ttt taa    ataaacaa      530
Leu Thr Lys Thr Ile Ala Asn Thr Tyr Phe Tyr Phe
            70                  75 ctttgatgat gtaacttgaa aaaaa                                          555
```

<210> SEQ ID NO 2
<211> LENGTH: 79
<212> TYPE: PRT
<213> ORGANISM: Homo sapiens

<400> SEQUENCE: 2

```
Met Ala Arg Ser Arg Leu Thr Ala Thr Ser Val Ser Gln Val Gln Glu
1               5                   10                  15

Asn Gly Phe Val Lys Lys Leu Glu Pro Lys Ser Gly Trp Met Thr Phe
            20                  25                  30

Leu Glu Val Thr Gly Lys Ile Cys Glu Met Leu Phe Cys Pro Glu Ala
        35                  40                  45

Ile Leu Leu Thr Arg Lys Asp Thr Leu Tyr Cys Glu Thr Gly Leu Ile
    50                  55                  60

Phe Leu Thr Leu Thr Lys Thr Ile Ala Asn Thr Tyr Phe Tyr Phe
65                  70                  75
```

<210> SEQ ID NO 3
<211> LENGTH: 16
<212> TYPE: DNA
<213> ORGANISM: Artificial Sequence
<220> FEATURE:
<223> OTHER INFORMATION: H-T11G anchored oligo-dT primer

<400> SEQUENCE: 3
aagctttttt tttttg    16

<210> SEQ ID NO 4
<211> LENGTH: 13
<212> TYPE: DNA
<213> ORGANISM: Artificial Sequence
<220> FEATURE:
<223> OTHER INFORMATION: arbitrary 5'13 mer H-AP 37

<400> SEQUENCE: 4
aagcttgggc cta    13

<210> SEQ ID NO 5
<211> LENGTH: 193

-continued

```
<212> TYPE: DNA
<213> ORGANISM: Homo sapiens

<400> SEQUENCE: 5
taactctaac gtgaacgcgg accaggaggc tggagtgcaa tggcgcgatc tcggctcact      60
gcaacctctg tctcccaggt tcaggaaaat ggctttgtaa agaagcttga gcctaaatct     120
ggctggatga cttttctaga agttacagga aagatctgtg aaatgctctt ctgtcctgaa     180
gcaatactgt tga                                                        193
```